(12) United States Patent
Fabian et al.

(10) Patent No.: US 7,579,484 B2
(45) Date of Patent: Aug. 25, 2009

(54) METHOD FOR THE PRODUCTION OF MONOALKYLAMINO KETONES

(75) Inventors: Kai Fabian, Wilhelmsfeld (DE); Claus-Peter Niesert, Seeheim-Jugenheim (DE); Joachim Kralik, Darmstadt (DE); Karl-Heinz Glüsenkamp, Essen (DE)

(73) Assignee: Merck Patent GmbH, Darmstadt (DE)

( * ) Notice: Subject to any disclaimer, the term of this patent is extended or adjusted under 35 U.S.C. 154(b) by 481 days.

(21) Appl. No.: 10/525,820

(22) PCT Filed: Aug. 1, 2003

(86) PCT No.: PCT/EP03/08514

§ 371 (c)(1),
(2), (4) Date: Feb. 25, 2005

(87) PCT Pub. No.: WO2004/020391

PCT Pub. Date: Mar. 11, 2004

(65) Prior Publication Data

US 2006/0122405 A1   Jun. 8, 2006

(30) Foreign Application Priority Data

Aug. 27, 2002   (DE) ................... 102 40 026

(51) Int. Cl.
C07D 333/06   (2006.01)
C07D 333/26   (2006.01)
C07D 307/36   (2006.01)
C07D 307/46   (2006.01)
C07D 307/56   (2006.01)

(52) U.S. Cl. ........................ 549/72; 549/498

(58) Field of Classification Search .............. 549/72
See application file for complete search history.

(56) References Cited

U.S. PATENT DOCUMENTS

| 3,859,305 A | 1/1975 | Posselt et al. |
| 4,948,813 A | 8/1990 | Wilkerson |
| 6,057,371 A | 5/2000 | Glennon |
| 6,103,910 A | 8/2000 | Hertel et al. |
| 2005/0256318 A1 | 11/2005 | Michel |

FOREIGN PATENT DOCUMENTS

EP   02015229.4   *   7/2002

OTHER PUBLICATIONS

Deeter, et al. Asymmetric Synthesis and Absolute Stereochemistry of LY248686, 1990, Tetrahedron Letters, 31, 7101-7104.*
Ohkuma, et al. General Asymmetric Hydrogenation of Hetero-aromatic Ketones, 2000, Organic Letters, 2, 1749-1751.*
Saakyan, et al. Studies on the chlorination of organic compounds and transformations of chlorinated derivatives. XIX. Aminomethylation of 2-acyl-3,4,5-trichlorothiophenes and the study of some reactions of Mannich bases. Armyanskii Khimicheskii Zhurnal (1984), 37, 261-5. Registry # 91707-96-9, indexed on STN on Nov. 16, 1984.*
CAPLUS: Registry No. 153871-87-5.*
Vippagunta, et al. Advanced Drug Delivery Reviews. 48 (2001) 3-26.*
Marc Devocelle, et al., Asymmetric Hydrogenation of α, β, and γ-Aminoketones Catalyzed by Cationic Rhodium(I){AMMPP} Complexes, SYNLETT, Jul. 11, 1997, pp. 1306-1308.

* cited by examiner

Primary Examiner—Rebecca L Anderson
Assistant Examiner—Shawquia Young
(74) Attorney, Agent, or Firm—Mullen, White, Zelano, Branigan, P.C.

(57) ABSTRACT

The invention relates to monoalkylaminoketones of the formula (I), in which $R^1$ and $R^2$ have the meanings indicated.

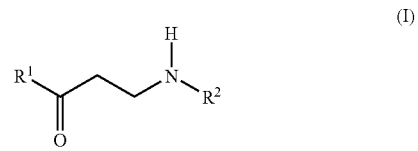

17 Claims, No Drawings

METHOD FOR THE PRODUCTION OF MONOALKYLAMINO KETONES

The invention relates to monoalkylaminoketones of the formula I

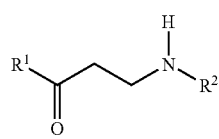

in which
R[1] denotes a saturated, unsaturated or aromatic carbocyclic or heterocyclic radical which is unsubstituted or mono- or polysubstituted by R[3] and/or R[4],
R[2] denotes alkyl having 1-20 C atoms,
R[3], R[4] each, independently of one another, denote H, alkyl or alkoxy having 1-20 C atoms, aryl, aryloxy or $COOR^2$, F, Cl, Br, OH, CN, $NO_2$, $N(R^2)_2$ or $NHCOR_2$, salts and solvates thereof, and to a process for the preparation thereof by reaction of compounds of the formula II

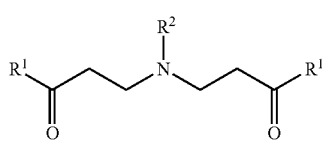

in which
R[1] and R[2] have the meaning indicated above, in the presence of an alkylamine of the formula $R^2NH_2$, in which R[2] has the meaning indicated above.

The compounds of the formula II are preferably employed as acid-addition salts, where, in particular, the acid-addition salts of strong acids, such as, for example, hydrohalic acid, methyl-, p-toluene- or benzenesulfonic acid, perchloric, sulfuric or phosphoric acid, are suitable. Particular preference is given to the hydrochlorides of the compounds of the formula II. On use of the acid-addition salts of the compounds of the formula II, the acid-addition salts of the compounds of the formula I are obtained, from which the free bases can be liberated by addition of a strong base, such as alkali metal carbonate or hydroxide.

The invention facilitates, in particular, the synthesis of precursors of optically active 3-monoalkylaminopropanols which are suitable as starting compounds in the preparation of medicaments, such as, for example, anti-depressants.

In particular, it opens up the possibility of obtaining in a simple manner 3-methylamino-1-(2-thienyl)-1-propanone, which can be used for the preparation of (S)-3-methylamino-1-(2-thienyl)-1-propanol. It is likewise possible to obtain 3-methylamino-1-phenyl-1-propanone, from which (S)-3-methylamino-1-phenyl-1-propanol can be obtained. These propanols can be, in particular, converted further, for example, into fluoxetine, tomoxetine and LY227942 (W. J. Wheeler, F. Kuo, J. Labeled Compd. Radiopharm. 1995, 36, 213-223).

In general, the synthesis of secondary amino ketones of the formula I under the conditions of a Mannich reaction (C. Mannich, G. Heilner, Chem. Ber. 1922, 55, 362-365) from compounds of the formula III and an alkylamine of the formula $R^2NH_2$ in the presence of a formaldehyde source, such as paraformaldehyde, acetals of formaldehyde, such as, for example, methyl or ethyl acetals, or trioxane, proves to be difficult since the secondary amino ketone of the formula I formed primarily serves directly as starting material for a subsequent second aminomethylation, where the main product obtained is the compound of the formula II:

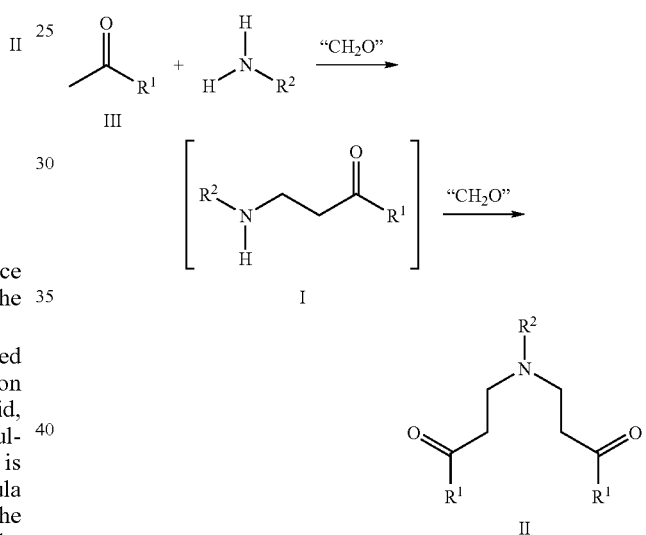

In particular, this applies to the reaction of acetylthiophene IIIa with methylammonium chloride in the presence of paraformaldehyde, which gives exclusively the dimer IIa and not the desired monomer Ia (F. F. Blicke, J. H. Burckhalter, J. Am. Chem. Soc. 1942, 64, 451-454):

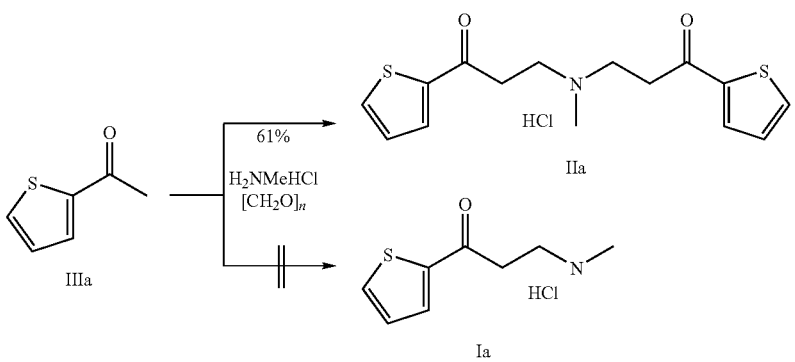

The invention was therefore based on the object of finding a process for the preparation of the compounds of the formula I or salts thereof and in particular of the compound Ia or salts thereof, which can be used, in particular, as intermediates in the synthesis of medicaments, which does not have the above-mentioned disadvantages.

It has been found that the compounds of the formula I and salts thereof, which are important intermediates for the preparation of medicaments, in particular of those which exhibit, for example, actions on the central nervous system, can be obtained by reaction of compounds of the formula II or salts thereof, in particular of compounds of the formula IIa or salts thereof, in the presence of an alkylamine of the formula $R^2NH_2$.

The present application preferably relates to the compound of the formula Ia

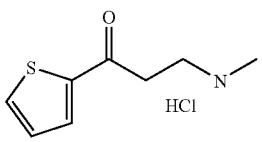

Ia

Preference is likewise given to the bases Ib and Ic which can be liberated, for example, by bases:

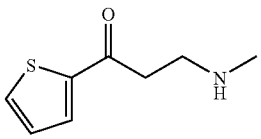

Ib

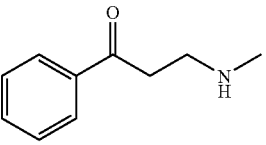

Ic and the salts obtainable by reaction thereof with acids and solvates obtainable by reaction with solvents.

Above and below, the radicals $R^1$, $R^2$, $R^3$, $R^4$ have the meanings indicated for the formulae I to II, unless expressly stated otherwise.

In the above formulae, alkyl has 1 to 20, preferably 1 to 6, in particular 1, 2, 3 or 4 C atoms. Alkyl preferably denotes methyl or ethyl, furthermore propyl, isopropyl, furthermore also butyl, isobutyl, sec-butyl or tert-butyl.

$R^1$ is preferably an aromatic carbocyclic or heterocyclic radical which is unsubstituted or substituted by $R^3$ and/or $R^4$. This radical may be mono- or polycyclic and is preferably mono- or bicyclic, but in particular monocyclic.

$R^1$ is particularly preferably unsubstituted.

If $R^1$ denotes a carbocyclic radical, this radical is preferably, for example, phenyl, o-, m- or p-tolyl, o-, m- or p-hydroxyphenyl, o-, m- or p-methoxyphenyl, o-, m- or p-fluorophenyl.

If $R^1$ denotes a heterocyclic radical, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2, 3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo[1,4]oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, for example, is preferably suitable.

It is likewise possible to use metallocenes, such as, for example, ferrocenes, in particular acetylferrocene.

The heterocyclic radicals may also be partially or fully hydrogenated. The heterocyclic radical used can thus also be, for example, 2,3-dihedral-2-, -3-, 4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, 4- or -5-pyrrolyl, 1-, 2- or 3-pyrrolidinyl, tetrahydro-1-, -2- or 4-imidazolyl, 2,3-dihydro-1-, -2-, -3-, -4- or -5-pyrazolyl, tetrahydro-1-, -3- or 4-pyrazolyl, 1,4-dihydro-1-, -2-, -3- or 4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or 4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, 4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo[1,4]oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

The said heterocyclic radicals may additionally be substituted by $R^3$ and/or $R^4$.

$R^1$ particularly preferably denotes phenyl or 2-thienyl.

$R^2$ preferably denotes methyl, ethyl, n-propyl or isopropyl, but in particular methyl.

$R^3$ and $R^4$, independently of one another, preferably denote H, methyl, in particular H.

Aryloxy preferably denotes, for example, phenyloxy, o-, m- or p-tolyloxy, o-, m- or p-hydroxyphenyloxy, o-, m- or p-methoxyphenyloxy, o-, m- or p-fluorophenyloxy.

Aryl preferably denotes, for example, phenyl, o-, m- or p-tolyl, o-, m- or p-hydroxyphenyl, o-, m- or p-methoxyphenyl, o-, m- or p-fluorophenyl.

The process according to the invention is simple, with the compound of the formula II preferably being dissolved or suspended in a solvent, such as, for example, water, alcohol, ether, saturated or aromatic halogenated or halogen-free hydrocarbons or mixtures thereof. The mixture is strongly acidified by addition of a strong acid, such as, for example, hydrochloric acid or sulfuric acid. A corresponding acid-addition salt of the alkylamine of the formula $R^2NH_2$ can optionally also be added to the solution or suspension of the compounds of the formula II.

The pH of the solution is subsequently increased to about pH 2-7.5, preferably pH 4-7, in particular pH 5.2 to 6.8, by addition of an alkylamine of the formula $R^2NH_2$, and the reaction mixture is warmed for a further 1 to 24 h, preferably 5-10 h, at 0° to 200° C., preferably at 10° C.-100° C. and in particular at 30° C.-90° C., giving the compounds of the formula I or salts thereof.

Particular preference is given to a one-pot process for the preparation of the compounds of the formula I, in which firstly the compound of the formula II is prepared by known processes, in particular in accordance with F. F. Blicke, J. H. Burckhalter, J. Am. Chem. Soc. 1942, 64, 451-454. In this process, a mixture of a formaldehyde source, such as, for example, paraformaldehyde or trioxane, is preferably reacted with a corresponding alkylammonium salt of the formula $R^2NH_2*HX$, in which HX stands for a strong acid, such as, for example, hydrogen halide, in particular hydrogen chloride, or sulfuric acid, with a ketone of the formula III and an excess of strong acid, such as, for example, hydrogen chloride, preferably in a solvent, such as, for example, water, alcohol or mixtures thereof. The reaction time of this reaction, depending on the conditions used, is generally between a few hours and 14 days, the reaction temperature is between 0° C. and 200° C., normally between 10° C. and 130° C., preferably between 20° C. and 100° C. and in particular between 30° C. and 90° C. The compounds of the formula II generally precipitate from the reaction mixture as a solid after the reaction.

The pH of the hitherto strongly acidic reaction mixture comprising the compounds of the formula II is subsequently increased to about pH 2-7.5, preferably pH 5-6, without further isolation of this compound by addition of an alkylamine of the formula $R^2NH_2$, and the reaction mixture is warmed for a further 1 to 24 h, preferably 5-10 h, at 0° to 200° C., preferably at 10° C.-100° C. and in particular at 30° C.-90° C., giving the compounds of the formula I. At high temperatures, the reaction is preferably carried out under superatmospheric pressure, preferably between 1 and 50 bar, in particular between 2 and 10 bar.

A suitable formaldehyde source is, in particular, trioxane.

A possible reaction mechanism is described below: firstly, the compound II is converted by thermal treatment into the vinyl ketone of the formula IV

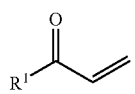

IV and the desired hydrochloride of the compound of the formula I. Owing to the presence of methylamine, the conversion of the vinyl ketone of the formula IV into the compound of the formula I takes place simultaneously "in situ", and the latter reacts again to give the desired hydrochloride of the compound of the formula I and the vinyl ketone of the formula IV.

In this manner, the compound of the formula II reacts approximately completely to give the desired product of the formula I, which can be isolated comfortably after re-acidification of the reaction mixture using, for example, conc. hydrochloric acid.

Suitable acids for the process according to the invention are, in particular, inorganic acids, preferably non-oxidising inorganic acids.

Preferred embodiments of the process according to the invention are mentioned below:

Process for the preparation of compounds of the formula I, characterised in that the pH for the conversion of the compounds of the formula II into the compounds of the formula I is adjusted to about pH 2-7.5 by addition of an alkylamine of the formula $R^2NH_2$.

Process for the preparation of compounds of the formula I, characterised in that the conversion of the compounds of the formula II into the compounds of the formula I is carried out at 0°-130° C..

Process for the preparation of compounds of the formula I, characterised in that the conversion of the compounds of the formula II into the compounds of the formula I is carried out at 0°-200° C., preferably under superatmospheric pressure in particular from 2 to 50 bar.

Process for the preparation of compounds of the formula, characterised in that firstly the compound of the formula II is obtained by reaction of a mixture of a formaldehyde source with corresponding alkylammonium salt and a ketone of the formula III in the presence of a strong acid, and the compounds of the formula II obtained in this way are employed without further isolation for the preparation of the compounds of the formula I.

Process for the preparation of compounds of the formula I, characterised in that the pH of the strongly acidic reaction mixture comprising the compounds of the formula II is increased to about pH 2-7.5, without further isolation of the compound of the formula II, by addition of an alkylamine of the formula $R^2NH_2$, and the mixture is subsequently warmed.

Process for the preparation of compounds of the formula, that the reaction mixture comprising the compounds of the formula II is warmed to 10° C. to 100° C. after addition of a corresponding alkylamine.

The process according to the invention is particularly suitable for the preparation of the ketones 3-methylamino-1-phenyl-1-propanone or 3-methylamino-1-(2-thienyl)-1-propanone, which can advantageously be converted further into the active ingredients duloxetine, fluoxetine, tomoxetine and LY227942.

The compounds of the formula II and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

If desired, the starting materials can also be formed in situ by not isolating them from the reaction mixture, but instead immediately converting them further into the compounds of the formula I.

Some of the compounds of the formula II are known; the compounds that are not known can easily be prepared analogously to the known compounds.

Suitable solvents are, for example, hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme), if desired also mixtures of the said solvents with one another or mixtures with water.

A base of the formula I, in particular Ib, can be converted into the associated acid-addition salt using an acid, for example by reaction of equivalent amounts of the base and the acid in an inert solvent, such as ethanol, followed by evaporation. Particularly suitable acids for this reaction are those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or poly-basic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, sodium carbonate, potassium hydroxide or potassium carbonate).

The invention furthermore relates to the use of the compounds of the formula I as intermediates for the synthesis of medicaments. Corresponding medicaments are mentioned, for example, in Synlett, 689-690, 1991.

The invention furthermore relates to the use of the compounds of the formula I as intermediates for the synthesis of medicaments which exhibit actions on the central nervous system.

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel.

EXAMPLE 1

A mixture of 49 g of trioxane, 111 g of methylammonium chloride, 162.2 g of acetylthiophene and 12 g of 37% hydrochloric acid in 176 ml of ethanol and 44 ml of water is refluxed for 17 h. 17.6 g of methylamine solution (40% in water) are subsequently added, and the mixture is warmed at 65-84° C. for 7 h. The reaction mixture is then allowed to cool to room temperature, 23.7 g of 37% hydrochloric acid are added, and the mixture is cooled to below 0° C. The deposited crystals are filtered off with suction, washed with acetone and subsequently dried, giving the desired ketone.

EXAMPLE 2

A mixture of 45.2 g of trioxane, 102.3 g of methylammonium chloride, 127.3 g of acetylthiophene and 10 ml of 37% hydrochloric acid in 242 ml of ethanol and 61 ml of water is refluxed for 19 h. The mixture is subsequently diluted with 400 ml of ethanol, 19.9 g of methylamine solution (40% in water) are added, and the mixture is again refluxed for 7 h. The reaction mixture is then allowed to cool firstly to room temperature and is cooled at −15° C. for 48 h. The deposited crystals are filtered off with suction, washed with 90 g of ethanol and subsequently dried in vacuo at 45° C. for 17 h.

EXAMPLE 3

A mixture of 113 kg of trioxane, 621 kg of methylammonium chloride, 400 kg of acetylthiophene and 35 kg of 37% hydrochloric acid in 783 kg of ethanol is refluxed for 19 h. The mixture is subsequently diluted with 992 kg of ethanol, 36 kg of methylamine solution (40% in water) are added, and the mixture is again refluxed for 4 h. The reaction mixture is then allowed to cool firstly to room temperature and is cooled at 5° C. for 48 h. The deposited crystals are separated off, suspended with 994 kg of ethanol at 68° C. and separated off again and dried in vacuo at 50° C. to constant weight, giving 363 kg of pure product.

The invention claimed is:

1. A monoalkylaminoketone compound of the formula I

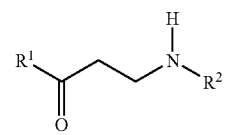

in which $R^1$ denotes a thienyl or furyl radical which is unsubstituted or mono- or polysubstituted by $R^3$ and/or $R^4$, provided that $R^1$ is not 3-thienyl substituted by both $R^3$ and $R^4$ where both $R^3$ and $R^4$ are methyl, $R^2$ denotes alkyl having 1-20 C atoms, $R^3$, $R^4$ each, independently of one another, denote H, alkyl or alkoxy having 1-20 C atoms, aryl, aryloxy or $COOR^2$, F, Br, OH, CN, $NO_2$, $N(R^2)_2$ or $NHCOR^2$, or a salt thereof.

2. Process for the preparation of a monoalkylaminoketone compound of the formula I

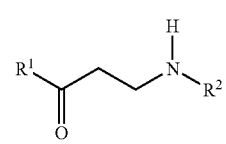

or an acid-addition salt thereof in which $R^1$ denotes a thienyl or furyl radical which is unsubstituted or mono- or polysubstituted by $R^3$ and/or $R^4$, provided that $R^1$ is not 3-thienyl substituted by both $R^3$ and $R^4$ where both $R^3$ and $R^4$ are methyl, $R^2$ denotes alkyl having 1-20 C atoms, $R^3$, $R^4$ each, independently of one another, denote H, alkyl or alkoxy having 1-20 C atoms, aryl, aryloxy or $COOR^2$, F, Br, OH, CN, $NO^2$, $N(R^2)_2$ or $NHCOR^2$, by reacting a compound of the formula II

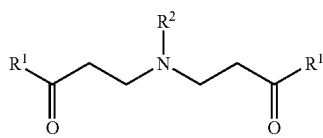

or an acid-addition salt thereof
in which
$R^1$ and $R^2$ have the meaning indicated above, in the presence of an alkylamine of the formula $R^2NH_2$, in which $R^2$ has the meaning indicated above.

3. Process according to claim 2, in which $R^1$ denotes 2-thienyl.

4. Process according to claim 2, in which $R^2$ denotes methyl, ethyl, n-propyl or isopropyl.

5. Process according to claim 2, wherein the pH for the conversion of the compounds of the formula II into the compounds of the formula I is adjusted to about pH 2-7.5 by addition of an alkylamine of the formula $R^2 NH_2$.

6. Process according to claim 2, wherein the conversion of the compounds of the formula II into the compounds of the formula I is carried out at 0°-200° C.

7. Process according to claim 2, wherein firstly the compound of the formula II is obtained by reaction of a mixture of a formaldehyde source with a corresponding alkylammonium salt and a ketone of the formula III

in which $R^1$ has the meaning indicated in claim 2, in the presence of a strong acid, and the compounds of the formula II obtained in this way are employed without further isolation for the preparation of the compounds of the formula I.

8. Process for the preparation of compounds of the formula I according to claim 6, wherein the pH of the strongly acidic reaction mixture comprising the compounds of the formula II is increased to about pH 2-7.5, without further isolation of this compound, by addition of an alkylamine of the formula $R^2NH_2$, and the mixture is subsequently warmed.

9. Process for the preparation of compounds of the formula I according to claim 7, wherein the reaction mixture comprising the compounds of the formula II is warmed to 0° to 200° C. after addition of a corresponding alkylamine.

10. Process according to claim 2 for the preparation of 3-methylamino-1-phenyl-1-propanone or 3-methylamino-1-(2-thienyl)-1-propanone.

11. Process according to claim 2, wherein an acid-addition salt of the compound of the formula II is employed, and an acid-addition salt of the compound of the formula I is obtained.

12. A compound of claim 1 which is of the formula Ia:

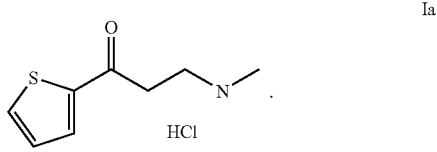

13. A compound of claim 1 which is of the formula Ib:

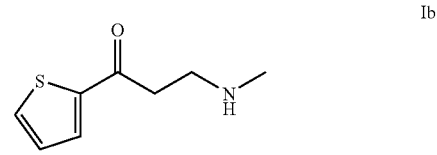

or a salt thereof.

14. A compound of claim 1, wherein $R^1$ denotes 2-thienyl.

15. A compound of claim 1, wherein $R^2$ denotes methyl, ethyl, n-propyl or isopropyl.

16. A compound of claim 1, wherein $R^1$ is selected from: 2- or 3-furyl, or 2- or 3-thienyl, each optionally substituted by $R^3$ and/or $R^4$.

17. A compound of claim 1, wherein $R^3$ and $R^4$ are both H.

* * * * *

UNITED STATES PATENT AND TRADEMARK OFFICE
CERTIFICATE OF CORRECTION

PATENT NO. : 7,579,484 B2  Page 1 of 1
APPLICATION NO. : 10/525820
DATED : August 25, 2009
INVENTOR(S) : Fabian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 480 days.

Signed and Sealed this

Fourteenth Day of September, 2010

David J. Kappos
*Director of the United States Patent and Trademark Office*